United States Patent [19]

Levengood

[11] Patent Number: 5,288,626

[45] Date of Patent: Feb. 22, 1994

[54] METHOD FOR PRODUCING NEW VARIETIES OF PLANTS

[76] Inventor: William C. Levengood, 4853 Wolf Lake Rd., Grass Lake, Mich. 49240

[21] Appl. No.: 539,302

[22] Filed: Jun. 15, 1990

Related U.S. Application Data

[63] Continuation of Ser. No. 363,451, Jun. 6, 1989, abandoned, which is a continuation of Ser. No. 907,858, Sep. 15, 1986, abandoned, which is a continuation-in-part of Ser. No. 545,656, Oct. 26, 1983, abandoned, which is a continuation-in-part of Ser. No. 309,607, Oct. 8, 1981, abandoned.

[51] Int. Cl.$^5$ .................... C12N 15/00; A01H 1/00
[52] U.S. Cl. .................... 435/172.3; 435/172.1; 47/58
[58] Field of Search ............ 47/1.3, 58, DIG. 1; 435/173.1, 173.3

[56] References Cited

U.S. PATENT DOCUMENTS 3,822,505  7/1974  Levengood .................... 47/1.3

OTHER PUBLICATIONS

Davis et al. 1980. *Microbiology*, Third edition, Harper and Row, Hagerstown, pp. 199-207.
J. Janick, *Horticultural Science*, 1972, WH Freeman and Co., San Francisco, p. 248.
Holl et al. 1974, in *Tissue Culture and Plant Science, 1974*, HE Street, ed., Academic Press, New York, pp. 301-327.
Webster's II New Riverside University Dictionary pp. 421-423 The Riverside Publishing Company USA.
Janick (1963) *Horticultural Science* 2nd ed. p. 248. W. H. Freeman & Co.
Holl et al. (1974) *Genetic transformation inplants*. Ins. Tissue Culture and Plant Science, Proceedings of the Third International Congress of plant tissue Culture. Editor Street. pp. 303-306, 308-311 & 320-322.

*Primary Examiner*—Gary Benzion
*Attorney, Agent, or Firm*—Ian C. McLeod

[57] ABSTRACT

A method for increasing the proportion of mutants in a generation in a first plant species having a recognized and established phenotype involves the simultaneous somatic exposure of germinal plants of the species to contact with whole cells and associated material of a second species of plants, and to electrophoretic conditions. The plants of the first species are preferably in a germinal state, such as seeds or seedlings, while the whole cells and associated materials of the second species can be a seedling root tip, a seedling, a tissue macerate (suspended in either water or agar) root nodules, fruit tissue or root tissue. When the cells of the first and second species have different membrane potentials, the step of electrophoretic exposure can be carried out by simply placing the cells in contact with one another. Preferably, however, an electropotential difference such as a constant DC voltage is disposed across the somatic cells of the first species of the plant and the whole cells and associated materials of the second species of plant, for example, by attaching one of a cathode and anode to the first species of plant, and the other of anode or cathode to the second species of plant.

25 Claims, 2 Drawing Sheets

METHOD FOR PRODUCING NEW VARIETIES OF PLANTS

This is a continuation of copending application Ser. No. 07/363,451 filed on Jun. 6, 1989 which application was a continuation-in-part of my then copending application Ser. No. 545,656 filed Oct. 26, 1983, now abandoned, which was in turn a continuation-in-part of then copending application Ser. No. 309,607, filed Oct. 8, 1981 and now abandoned.

BACKGROUND OF THE INVENTION

1. Field of the Invention

The present invention relates to a method for inducing mutations in plants, and more particularly to a method for increasing the number of plants of a first species which exhibit a phenotype or characteristic normally associated with a different species.

2. Description of the Prior Art

The members of a given species of plant typically share a number of well-established physical characteristics associated with the genetic materials of their cells; these characteristics are known as phenotypes. However, it is well known that plants of a given species having one or more new and distinctive characteristics, generally referred to as sports or mutations, occur naturally as a small fraction of any plant population. For centuries, mutants have been selectively bred to produce new varieties or modifications of existing plants. In natural populations of plants, however, the frequency of mutations is generally considered to be less than 1 in 500,000, so that the selection of desirable mutants after such breeding is a slow and laborious process, particularly since it is well recognized that mutants exhibiting a desirable phenotype are rare, and progeny outputs are often low.

Several methods for increasing the occurrence of mutants in a population of a given species are well known; for example, the exposure of such a population to ionizing radiation. Such techniques, however, are typically subject to the drawbacks that the individually resulting mutants are generally weak, and must still be subjected to the time-consuming and labor-intensive techniques of isolation and selective breeding for a large number of generations, before a sufficient number of mutants possessing the new phenotype are obtained for use in outcrossing or agricultural growth.

Recombinant DNA and protoplast fusion techniques are potentially useful for producing new varieties of plants without isolation of mutants or selective breeding. The use of these techniques is subject to several drawbacks, however. First, these techniques are tedious and slow, requiring elaborate instrumentation involving a large number of chemical processes, and a substantial investment in the education and training of the personnel conducting the procedures. Presently, these techniques are very expensive and time consuming. Indeed, Applicant is aware of no reported instance of the inducement of a functional expression of a novel gene (phenotype) from one species of plant to a population of another species of plant, employing these genetic engineering techniques.

SUMMARY OF THE PRESENT INVENTION

The present invention overcomes these and other difficulties encountered in prior methods of inducing mutations in a population of a first species of plant by providing a method for increasing the number of mutants exhibiting altered phenotypic characteristics, characteristics which are stable in successive generations, where such phenotypic characteristics are an established trait of a second different species of plant. The method of the present invention allows for the production of large numbers of plants having substantial modifications from the parent generation, without the delay of several generations for selective breeding and establishment of characteristics as stable by outcrossing, and which does not require the complex instrumentation or large numbers of chemical reactants and steps inherent in present recombinant DNA or protoplast fusion techniques.

The method according to the present invention involves placing a plurality of germinal plants of a first or recipient species, this first species exhibiting at least one established phenotype, in contact with the whole cells and associated materials of a second species of plant, while exposing the germinal plants of the first species to electrophoretic conditions, such as an ionophoretic current. The germinal plants are grown to adult plants, or to a stage sufficient to observe any changes from the established phenotype. The exposure of the germinal plants of the first species to electrophoretic conditions can be carried out by simply abutting a portion of seedlings of the first species with seedlings of a second plant species, when the cells of the first and second species have differing membrane potentials. This can be carried out by excising complimentary sections from the root of seedlings of the first and second plant species, and abutting the cut surfaces of the roots. Preferably, however, an external DC current is applied across the germinal first species plants and whole cells and associated materials of the second plant species by attaching an anode to the plants or materials of one species, and a cathode to the plants or cells of the other species. Typically the plants and materials are exposed to a constant DC voltage having a current density in the range of 10 to 100 microamps per centimeters applied at a potential difference of from 1 to 50 volts for periods of five minutes to 24 hours. In effect, the donor material of the second species acts as an electrode substrate or base contactable with the seedlings of the first species. The donor material is prepared as either a tissue macerate or as whole tissue. The donor material can be placed on sterile cotton or a filter paper which in turn rest on a stainless steel plate electrode. Most preferably, the acceptor tissue or plants of the first species are exposed at the seed or early seedling stage, typically 24 to 96 hours after germination by placing the root apex in contact with the donor-coated electrode, and the shoot apex, cotyledons or coleoptile in contact with the electrode of opposite polarity.

The method of the present invention is preferably carried out with genetically pure, stable and homozygous inbred varieties of lines as the host or acceptor first species. Such well-established lines were used in all of the examples described below, and are commercial varieties which have been released from university or USDA breeding programs for public use.

After exposure, the test seedlings or germinal plants of the first species, along with untreated controls, are developed to maturity under field conditions or in a greenhouse, depending upon expediency. Typically, alterations are observed in the growth rates and yields of the germinal plants actually treated, depending upon the type of donor and the exposure parameters; however, a stable expression of an altered phenotype is typically not seen until at least the second generation bred from the treated plants. The frequency of inherited, varietal alterations resulting from the present method ranges from 5% to 95% of the test population, typically, depending upon the specific procedure and plant species involved. This is a substantial improvement over the proportion of one in a few thousands or several thousands of cells or plants treated by recombinant DNA and protoplast fusion methods.

Not only does the present method yield a significantly increased proportion of mutants in the treated plants, but a significant proportion of the resulting mutants exhibit an altered phenotypic characteristic which was, in fact, an established phenotypic characteristic of the second or donor species of plant. It is believed that this transferred phenotype results from the transduction of genetically associated cell tissue components and macromolecular complexes from the second or donor species into the intact, somatic cells of the first or acceptor species, in such a manner as to alter the genotype and/or phenotype of the plants of the first species. For this reason, plants treated in accordance with the method of the present invention, or grown from plants treated in accordance with the present invention, are designated by generation with the letter "T". For example, the first treated generation of the first species of plant is described as the T-1 generation, while a second inbred generation grown from the adult plants of the T-1 generation are referred to as the T-2 generation. This designation of generations is intended to avoid confusion with the system of F-1, F-2 and so on, normally employed in conventional plant breeding, when crossing for hybrid vigor.

It is thus an object of this invention to provide a method, by means of electrophoresis techniques, for the production of new plant mutations consisting of types and varieties having altered genotypic and/or phenotypic characteristics, that is simple when compared with the recombinant DNA and protoplast fusion methods known in the art. The methods of the present invention do not require complex instrumentation, nor drastic alterations in cell wall-membrane contiguity, particularly the removal of the cell wall as required by prior techniques, or detailed elucidation of chromosome maps.

Another object of the present invention is to provide a method for the production of new varieties of plants that can quickly yield large numbers of healthy plants having substantial modifications from the parent plants, thus eliminating the delay of several generations and large test populations required in prior selective breeding programs, which have been conventionally necessary before the plants can be used in out-crossing. Both conventional breeding programs and the recombinant DNA and protoplast fusion methods generally produce a low yield of mutants which must be selectively grown and bred for a large number of generations, before a sufficient number of stable plants are available for use in programs for developing plant varieties; in contrast, the production of such stable plant varieties is remarkably more rapid in the present invention.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which.

DETAILED DESCRIPTION OF THE PREFERRED EMBODIMENTS OF THE PRESENT INVENTION

The method of the present invention both increases the proportion of mutants in a generation of a first species of plant (the species having at least one established phenotype) while simultaneously causing at least some of the resultant mutant plants to exhibit a phenotype, characteristic or trait of a second species of plant. Several illustrative techniques and specific examples of the present invention are described hereinafter. It should be understood that the technique of the present invention is generally intended to be used on a substantial number of plants sought to be modified, so as to provide a ready supply of mutant plants for subsequent varietal development. The electrophoretic techniques described however, can also clearly be conducted on a single plant cell as the acceptor, employing micromanipulative techniques in order to apply an ionophoretic current across the single acceptor cell and donor material. Such a technique is, of course, within the scope of the present invention. In such a case, the acceptor electrode can comprise a thin needle or wire inserted into or in contact with the acceptor cell. In all cases, however, the cell wall and plasmalemma are preferably not breached by the present method.

It is believed that germinal plants, such as seeds or seedlings about one to five days after germinations, are most susceptible to successful treatment by the method of the present invention. While some variation may occur in the percentage of mutant plants grown from the treated seeds or seedlings, such as percentage varying with the species of plants used and the particular technique employed, the method of the present invention will generally result in a substantially greater percentage of mutations than results when radiation or the like are employed to create mutant plants. Moreover, whereas radiation and the like cause random mutations having widely varying characteristics, in general a substantial percentage of mutants formed by this invention tend to exhibit substantially similar characteristics.

Figure 1:
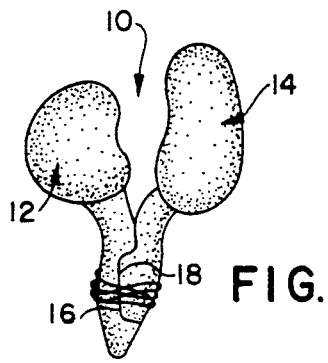
FIG. 1 depicts a joined pair of seedlings of two species of plant.

With reference first to FIG. 1, a first embodiment of the method of the present invention is thereshown involving a joined pair of seedlings 10 of two different species of plants. One or more seedlings 12 of first species of plant are prepared by longitudinally excising a section consisting of about one-half of the root's side, to expose a fresh cut surface 16. Preferably, the germinated seedlings include radicles in the range of 1 to 6 centimeters in length, and the radicle tip is left intact when the surface is cut, exposing the procambium, protophleom and protoxylem cells. The root side and tip of a corresponding number of seedlings 14 of a second, different species of plant are excised, the radicle tip as well as the longitudinal portion of the side being removed, to form a cut surface 18. The seedlings 14 of the second species are preferably of similar radicle development as the seedlings 12 of the first species, and the procambium, protophloem and protoxylem of the seedlings 14 of the second species similarly form the cut surface 18.

The cut surfaces 16 and 18 of the two species of plants are then immediately abutted and a thin cord is wrapped or tied about the abutted roots in order to insure good contact between them and maintain them in abutment. The excisions on each of the seedlings 12 and 14 should be complementary in order to maximize contact between the cut surfaces 16 and 18. The joined seedlings 10 are planted and nurtured to adult plants, at which time either seeds from the plants are harvested for growth of a T-2 generation from which plants having desired traits are selected; or the T-1 adult plants are directly selected for desired traits. The former is the particularly preferred procedure in this invention.

In the embodiment disclosed in FIG. 1, the seedlings 14 of the acceptor species are exposed to electrophoretic conditions through the existence of a difference between the natural membrane potentials known to exist about both plant and animal cells, Jaffe, Nature, 256: 600-602 (1977). Although natural membrane potentials are known to be of low magnitudes, generally on the order of 1 to 100 millivolts, the adjacent disposition of cells of different species will result in a mutual electrophoretic process. Because each plant species has its own distinctly characteristic metabolic cycle and timing of activity, the biochemical cycles in plants 12 of one species will likely be at a phase different from that of plants 14 of the second species. Consequently, since at one growth stage the mutual potentials may be complementary and at another stage of development they may be opposed, this can provide a potential gradient quite different from that which the cells of the plants 12 of the first species would experience under normal conditions of development.

Because the plant radicle or root tip is responsible for the production of vitamins and other important enzymes used in the development of germinal plants, the plant 14 having the root tip excised will be acceptor plant, while the plant 12 having the root tip retained will be the donor plant.

Applicant has measured the current density in the region where the cut tissues contact, when abutted as disclosed in FIG. 1. For example, when four day old seedlings from different species such as corn and soybean are paired, the current density reaches a maximum value of about 0.7 microamperes per square centimeter at about 40 minutes after initial abutment, with a very gradual decline over the next 10 hours. In contrast, when seedlings of the same species are paired in a similar fashion, such as soybeam-soybean pairings, the current density is only around 0.01 microamperes per square centimeter, again showing a very gradual decline with time. Typically, even at this low electric potential difference between the seedlings of disparate species, new traits appear in the acceptor plants at about a 5% mutuation level and are often in the nature of phenotypical alterations such as plant shape, size and foliage color. The T-1 generation is then selfed to yield a T2 generation, and the altered phenotypes exhibited by the mutated members of the new generations do not segregate out in succeeding generations.

Figure 2:
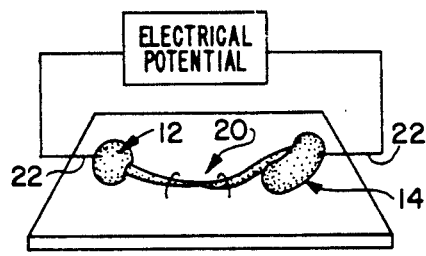
FIG. 2 depicts a joined pair of seedling with root tips excised and electrodes inserted.

With reference now to FIG. 2, a second preferred embodiment of the invention is thereshown in which the natural membrane potential difference between seedlings of two different species is augmented or reversed, as desired, by the application of an ionophoretic current across the joined seedlings. More particularly, the root tips of seedlings 12 and 14 of two different species are excised, and the cut portions of the seedlings abutted together. A pair of electrodes 22 are then afixed to the seedlings 12 and 14 generally opposite the abutted root portions, for example, in the shoots or cotyledons. An electrical potential such as provided by a constant direct electrical current is then applied through the electrodes 22 across the pair of joined seedlings 20. The voltage applied to the seedlings will generally range between 1 to 45 volts, and preferably on the order of 1.5 to 22.5 volts, for times of about 5 minutes to 24 hours, and preferably about 5 minutes to about 3 hours. This yields a current density across the region where the cut seedlings abut one another in a range of about 10 to 100 microamperes per square centimeter. Preferably, the direction of current applied is chosen to augment the difference in membrane potential of the cells between the different species of plants. Once subjected to such a potential, the seedling pairs 20 are then separated into individual seedlings 12 and 14, which are separately nurtured to adult plants. The selfed T2 generation from the treated T1 generation plants are then selected for desired traits.

Preferably, the electrodes 22 are constructed from iron, since iron electrodes can be inserted into the seedlings without causing detrimental effects to the seedlings. Other electrodes which are not deleterious to plants can also be used, and stainless steel electrodes are particularly preferred for this purpose.

Figure 3:
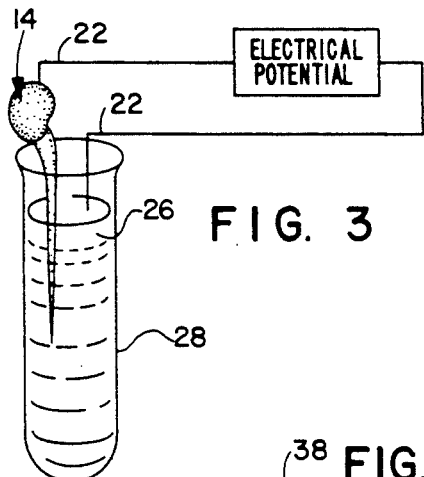
FIG. 3 depicts an electrical potential applied to a seedling in contact with a treated medium.

The donor material employed in the present invention need not be a whole plant or seedling. Instead, as shown in FIG. 3, tissues of a donor species of plant can be macerated, such as by blending in water, in order to produce an aqueous donor liquor. The aqueous liquor is collected and added to a support medium such as agar or gelatin, to produce a treated medium 26. The treated medium 26 is disposed in a test tube or vial 28, or other convenient container, and the root tip of the seedlings 14 of the second species of plant are placed in contact with or immersed in the medium 26. Most preferably, the radicle of the acceptor plant seedling 14 is placed in the medium. Once electrode is contacted with the shoot of the seedling, while another electrode is disposed in contact with the support medium 26. An electrical potential is then applied across the seedling 14 and medium 26, of the type, time and intensity described in the preceding embodiment. Following the application of this electrical potential, the seedlings 14 are removed from the treated medium 26 and grown to adult plants, which are then either selected for desired traits or are selfed in order to determine which traits in a T2 generation are inheritable and stable.

Figure 4:
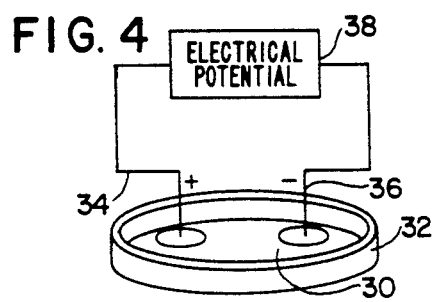
FIG. 4 depicts the application of an electrical potential to a liquor derived by macerating plant tissue.
Figure 5:
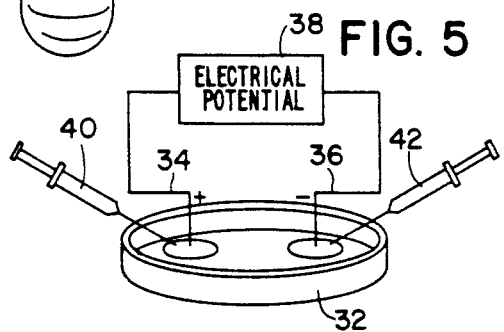
FIG. 5 depicts fractionation of electrode solutions surrounding electrodes.
Figure 6:
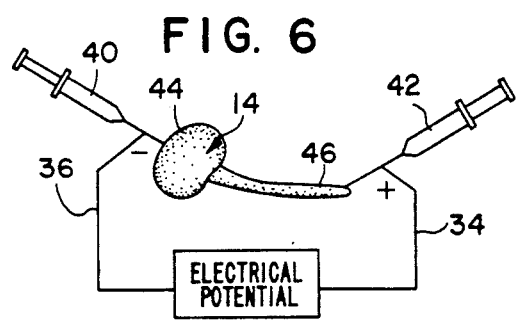
FIG. 6 depicts the application of an electrical potential across a seedlings and solution filled syringe.

The use of agar or gelatin as a medium 26 for suspending the aqueous liquor is desirable, but not essential to use of an aqueous liquor of the donor plant cells. In the embodiment shown in FIG. 3, the medium can be replaced by the aqueous liquor itself. Moreover, the aqueous liquor can itself be subjected to an electrical potential prior to its contact with the acceptor seedling 14, as shown in FIGS. 4 through 6. As above, the tissue of the donor species of plant is macerated in distilled water, and the resulting liquor 30 collected. The aqueous liquor 30 is then deposited in a petri dish 32, and a positive electrode 34 and a negative electrode 36 are placed in the aqueous liquid 30. An electrical potential 38 is then applied to the aqueous liquor 30 across the positive electrode 34 and the negative electrode 36. While the electrodes can be constructed from silver, it is preferred that the electrodes are constructed from platinum in order to reduce oxidation of the electrodes, and minimize the effect of the electrode material upon the aqueous liquor 30. Generally a potential of about 5 to 20 volts is applied for a time of about 10 to 30 minutes. Consitutents of the aqueous liquor will migrate towards or away from one or the other of the electrodes 34 and 36, depending upon the charge possessed by the various tissue constituents. As shown in FIG. 5, the portion of the aqueous liquor 30 which is located about the anode or positive electrode 34 (the anode solution) is removed from the remainder of the aqueous liquor 30 by withdrawal into a hypodermic syringe 40. The portion of the liquor 30 surrounding the negative electrode or cathode 36 (the cathode solution) is removed by drawing into a syringe 42.

The syringes 40 and 42 containing the anode and cathode solutions are then inserted into opposite ends of seedlings 14 of the acceptor species, as shown in FIG. 6, and pressure is applied to the syringes 40 and 42 to inject a portion of the anode and cathode solutions to the tissue of the seedlings. For example, the anode solution contained in the syringe 40 can be inserted into the shoot 44 of the seedling 14, while the cathode solution contained in the syringe 42 can be injected into the root of the seedling 14, preferably into the radicle 46. The positive electrode 34 and negative electrode 36 are then connected to the syringes 42 and 40, respectively (opposite to the electrodes from which the syringes collected a portion of the aqueous liquor), the syringes preferably having metal tips to facilitate electrical contact with the seedling 14. A potential difference of about 1 to 50 volts and preferably of about 1.5 to 22.5 volts is applied to the seedling through the syringes for a time of about 5 minutes to 24 hours, and preferably for about 5 minutes to about 3 hours. Subsequent to the application of the potential difference, the needles are removed from the seedling 14, and the seedling 14 grown to an adult plant. A plurality of seedlings are selected for the desired traits in either the T1 or T2 generation, as described earlier.

Figure 7:
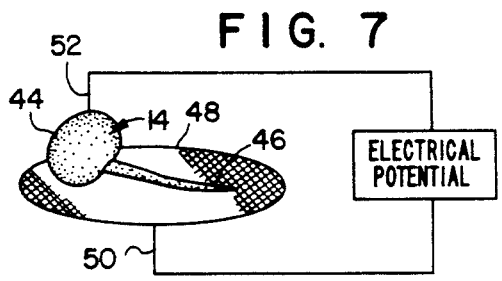
FIG. 7 depicts the application of an electrical potential across a seedling disposed on a treated filter paper.

In another preferred embodiment of the present invention, only one of the electrode solutions needs to be applied to the acceptor species of plant in order to obtain the high proportion of mutations encountered in the present invention. With particular reference to FIG. 7, either of the anode or cathode solutions collected by the syringes 40 and 42 can be applied to a porous medium, such as a filter paper 48. A seedling 14 of the acceptor species of plant is positioned on the filter paper 48 with both its radical 46 and its shoot 44 in contact with the filter paper 48 containing the donor electrode solution. The donor-containing filter paper 48 is placed in contact with a first electrode 50 while a second electrode 52 of opposite polarity is inserted into the shoot 44 of the seedling 14. As above, the polarity of the electrode 50 in contact with the filter paper 48 is opposite to the sign of the electrode 40 or 42 from which the anode or cathode solution was collected. Because at least some of the constituents of the anode or cathode solution will be of the type to migrate towards the electrode opposite in sign so that of the electrode 50 in contact with the filter paper, these constituents will tend to migrate towards the second electrode 52 upon the application of the potential difference across the electrodes 50 and 52, and thereby across the seedling 14. The length of time and type and strength of potential difference applied across the seedling 14 are as disclosed above. Subsequent to the application of the potential difference, the electrodes 50 and 52 are removed from the seedling, and the seedling 14 grown to either the T-1 or T-2 generation, and selected for any desired traits. The electrodes 50 and 52 are preferably constructed of iron or stainless steel, because of their minimal effects on biological systems.

Figure 9:
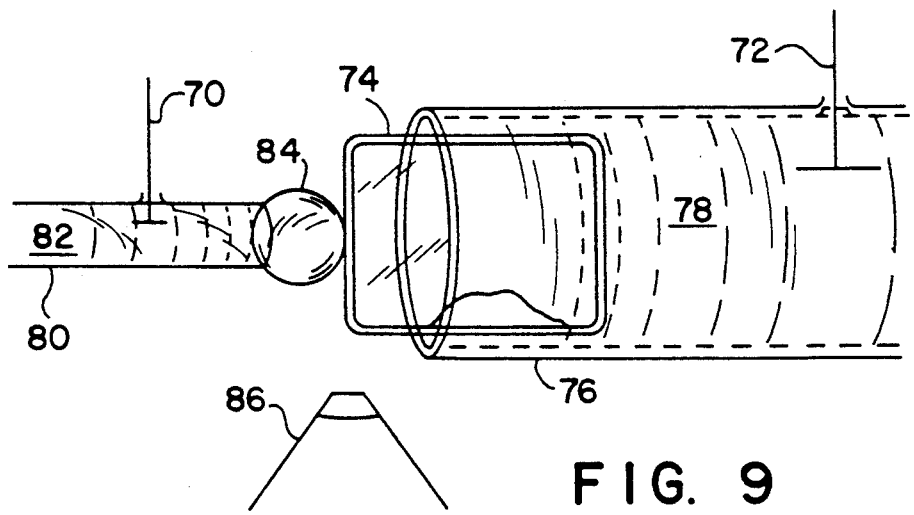
FIG. 9 depicts the application of an electrical potential across a single cell and a donor medium.

It should be evident that the embodiments disclosed in FIGS. 3 and 7 are readily adaptable to use in exposing a single cell or isolated protoplast cell of an acceptor species to the aqueous liquor or cathode or anode solutions from the donor species. More particularly, in FIG. 9 there is disclosed another preferred embodiment of the present invention in which a pair of non-reactive electrodes 70 and 72 (preferably platinum electrodes) are used to place an electrical potential across a single plant cell or isolated protoplast 74. The cell 74 is carried on the end of a glass tube 76, the tube 76 being filled with water 78 or another conductive liquid so as to permit manipulation of the cell 74 within the tube 76. The use of a water-filled tube to carry a single plant cell is, of course, a known micromanipulative technique. One of the electrodes, for example, the cathode 72, is electrically connected through the tube 76 and disposed in contact with the liquid 78 in the tube 76. The other of the electrodes, for example, the anode, is electrically connected through the wall of another glass tube 80 and disposed in contact with a donor medium 82 contained in the tube 80. The donor medium 82 is the same as the media prepared in accordance with the preceeding embodiment of the invention. Pressure is applied to the medium 82 to express a small droplet 84 of the medium 82 out of the end of the glass tube 80. The tubes 76 and 80 are mounted to a micromanipulator (not shown), which aligns the tubes 76 nd 80 and permits the droplet 84 to be brought into contact with the plant cell 74. Alignment and contact can be visually monitored through a microscope 86. The plant cell 74 is then subjected to electrophoretic conditions by the application of a DC voltage across the electrodes 70 and 72. The applied voltage should be sufficient to produce a current density in the range of 1.0 to 100 microamps per square centimeter, for a time of about minutes to three hours.

Figure 8:
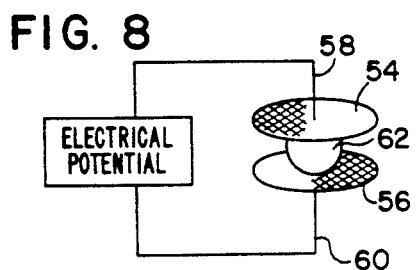
FIG. 8 depicts a seed disposed between two pieces of treated filter paper with an applied electrical potential.

A final preferred embodiment of the general method of present invention is shown in FIG. 8 in which a seed 62 of an acceptor species of plants id disposed between two pieces of porous material or filter paper 54 and 56.

Cathode and anode solutions of a tissue macerate of a donor species are prepared as described above. The filter papers 54 and 56 are placed on electrodes 58 and 60, and infused with the anode or cathode solution collected from the electrode 34 or 36 of potential opposite to the electrodes 58 and 60. One of the filter papers 54 or 56 is placed in contact with the hilum or embryo end of the seed 62. The electrodes 58 and 60 can be constructed of various materials, preferably stainless steel or other iron material. It is preferred that the electrodes do not contact the seed 62 directly. An electric potential is the applied to the electrodes 58 and 60, and thus applied across the seed 62. The potential can be applied to the dry seed 62, or the seed can be allowed to be partially or completely imbibed with water or the anode and cathode solutions, before the potential difference is applied. A constant direct current of 20 to 90 volts is applied to the dry seeds, or a potential of 1 to 40 volts is applied to the partially imbibed seeds, for about 5 minutes to 1 hour. After such treatment, the seed may be returned to the quiescent state and stored until it is convenient to plant them. Alternatively, the seeds may be germinated immediately, sprouted and grown to adult plants. Adults in the T2 generation, selfed from the T1 plants, are selected for desired traits.

The methods of the present invention are further illustrated by several following examples. Some of the examples have been followed through the T5 generation in extensive agricultural testing. In general, it has been found in the invention that the induced mutations recognizably segregate in the T2 or subsequent generations, so that selections for further crossings or further development can accordingly be made in the T2 generation. For the most careful screening of the types of mutations, it has been fund advantageous to examine plant row tests in the T2 generations, that is, to use seeds from the individual treated plants of the T1 generation for inbred or selfed plant row replications, in the T2 generation testing. This allows a more efficient screening and categorization of the induced mutations from the T1 generation since traits or characteristics which are not reproduced in a selfed or inbred generation are neither stable nor of particular commercial value.

The high percentage of mutants obtained in the method of the present invention allows a relatively small number of seeds or seedlings to be treated in the T1 generation (which is also referred to as the transduced series), on the order of 15 to 20 seedlings of each transduction polarity being examined for differences in growth and for phenotypic variations, along with a control group of untreated seedlings or seeds of equal number. Thus, about one-third of the plants field tested at the time of the T1 generation are control plants. After the T1 generation, each of the treated lines and controls are grown in three replicated rows of 40 to 50 seeds each within statistically randomized test plots. Unless otherwise indicated, the Latin Square method of randomization was employed. Subsequent to the T2 generation the lines are selected and expanded according to the apparent importance of the new characteristics of the mutant plants.

The acreage necessary to adequately insure that the new characteristics are stabilized in the particular treated lines will vary according to the percentage of mutants obtained in the T1 generation and the number of lines that appear desirable to investigate. For example, in 1984, applicant produced T1 transduced series of acceptor species including corn, tomato, soy beans and navy beans. Less than a one acre test plot was required for 124 transduction series and controls. These particular tests were made in lower Michigan. By 1985, the subsequent T3 generation testing involved an area of 10 acres, while the 1986 T5 generation required over 70 acres of primary growth, in addition to replicated tests at several locations and in several states. The T2 and T4 generations of these transduced series were seed expansion grow-outs in Hawaii, in order to shorten the time necessary to achieve the T5 generation.

The following examples serve to further illustrate the present invention:

EXAMPLE ONE

Longitudinal sections from soy bean (*Glycine max*) seedling roots (the donor species) were excised in a plurality of seedlings, and longitudinal sections including the root tip were excised from a plurality of bush bean (*Phaseolus vulgaris*) seedlings (the acceptor species). Each seedling has a radicle in the range of 1 to 6 centimeters in length, and the excised portions were of complementary shape, such as to expose the procambium, protophloem and protoxylem cells of each root tip. The cut portions of pairs of seedlings of the different species were abutted and bound with thread, as shown and described in conjunction with FIG. 1. The pairs of joined seedlings were grown to adult plants.

One in twenty bush bean seedlings so treated resulted in an adult plant that was shorter than the control plants and which has more compact foliage than the control plants, characteristics which are of commercial importance in the harvesting of bush beans. Tall plants tend to lodge and intertwine, and are thus less efficiently harvested. These plants also had leaves of a deeper green color than the control plants, the fruit of these plants and these plants exhibited greater drought resistance than the control plants. Yields under field condition, however, were found to abe about the same as those of the control plants. The seeds of these plants were observed to be intermediate in shape between the soy bean and bush bean progenator seeds.

These new characteristics were stable; they were observed without change through seven inbred or selfed generations with no reversion back to the height, bushiness, color, sweetness, and drought resistance of the original and control bush bean plants. Six generations of the mutated plants, along with an equal number of controls, were grown under field test conditions as described earlier. The maintenance of these characteristics for seven generations demonstrates that the changes were inheritable. The fact that the inbred, transduced plants do not segregate or revert, that is, return to the characteristics of the control plants, demonstrates that the method can provide new varieties of plants which breed true. As will be subsequently discussed, this non-segregating, stable nature of the growth alterations suggests a non-Mendelian or cytoplasmic type of inheritance.

EXAMPLE TWO

Longitudinal sections from a plurality of bush bean seedlings (*Phaseolus vulgaris*) roots, the donor species, and longitudinal sections including the root tips from soy bean (*Glycine max*) seedlings, the acceptor species, were excised to expose procambim, protophlem and protoxylum cells on each seedling. Each seedling was germinated and possessed radicles in the range of 1 to 6 centimeters in length. The excised portions of pairs of seedlings of different species were cut in complementary shapes, and the exposed cut portions of the seedlings were joined together to form pairs of joined seedlings in the fashion shown in and described in conjunction with FIG. 1. Each pair of joined seedlings contained a bush bean seedling and a soy bean seedling. The pairs of seedlings were then grown to adult soy bean plants, and one in ten of the soy bean plants so grown exhibited seeds that were intermediate in shape and color between the seeds of the bush bean and the soy bean progenators. The leaves of the one in ten altered soy bean plants were less lobed in shape than the leaves of the control plants, the stem node lengths were reduced as compared to those of the soy bean control plants, and the number of stem nodes was increased as compared to the controls as well. This resulted in a line of altered soy bean plants which had more compact foliage than the control plants and was thus more resistant to lodging under field conditions. These changed characteristics were maintained in inbred or selfed plants grown through four generations. Three of these generations were grown along with an equal number of controls under field conditions.

This example is, of course, the reciprocal or reverse of the transduction which occured in Example 1, that is, the donor and acceptor species are reversed. Significantly, the percentage of altered or mutated plants obtained is of the same order of magnitude in each example, demonstrating that the method allows modifications to be made to plants in two directions. Typically, attempts to induct positive and viable mutations in plants by conventional methods such as by chemical or ionizing radiation treatments yields an expected frequency of useful, viable mutations or phenotypic alterations of one in five hundred thousand test plants (a frequency equal to 0.000002). Examples 1 and 2 demonstrate that the method of the invention can produce plants having new, inheritable characteristics at a rate of 25,000 times that expected under conditions of conventional chemical or radiation treatment. This increase in the rate of mutation is highly significant and commercially valuable in terms of time, space, and the volume of plants needed to be treated or exposed in order to produce positive mutations.

EXAMPLE THREE

Tissue from the immature fruit of tomato (*Lycopersicon esculentum*) was macerated in distilled water and the resulting aqueous liquor placed in a perti dish. A pair of spaced silver electrodes were inserted in the macerate liquor and a constant direct current electrical potential of 9 volts was applied for 20 minutes. A portion of the liquor surrounding each electrode was drawn into a hypodermic syringe having a conductive needle tip. The conductive syringe tips were inserted into the root and shoot of a plurality of soy bean (*Glycine max*) seedlings in the fashion shown in and described in conjunction with FIG. 5, 6 and 6, above. A negative electrode was then connected to the syringe containing the solution which has surrounded the positive electrode in the petri dish, while a positive electrode was connected to the syringe containing the other electrode solution. A constant DC electrical potential of 22.5 volts was then applied for five minutes, so that a current of approximately 100 microamps was passed through the seedlings.

Two series of 20 seedlings were treated and grown along with 20 non-treated controls. In one treated series, the electrode solution from the positive electrode in the petri dish was applied to the seedling roots. In the other series, the electrode solution from the negative electrode in the petri dish was applied to the roots of the seedlings. After such treatments, all of the seedlings were grown under field test conditions as described above, and the results obtained are given in Table I below. The asterisk indicates data which is statistically significant at about a 95% confidence level (P less than 0.05). The observed increases in pod and seed yields continued in two subsequent generations of selfed or inbred plants, grown under field test growth conditions.

TABLE I

| | (N = 20 plants per series) | | |
|---|---|---|---|
| ELECTRODE SOLUTION APPLIED TO ROOT | PODS PER PLANT AVERAGE | S.D. | AVERAGE SEED YIELD (GRAMS PER PLANT) |
| ANODE (+) | 59.1* | 43.6 | 16.76 |
| CATHODE (−) | 49.6* | 36.7 | 14.06 |
| CONTROLS | 32.5 | 13.7 | 9.50 |

EXAMPLE FOUR

A portion of root tissue from Eastern Marsh Cabbage Plant (*Symplocarpus foetidus*) was excised in early Spring (mid-March), macerated in distilled water and admixed with a sufficient quantity of agar to create a donor macerate of moderate viscosity. A portion of this donor macerate was placed in a test tube. The radicles of a plurality of tomato seedling (*Lycopersicon esculentum*) were immersed in the donor medium. One electrode was inserted into each of the seedlings, while another was positioned in contact with the donor medium. A direct current 9 volt potential difference was applied across the electrodes, and thus across the seedlings and macerate, for five minutes.

Tomato is well known to be one of the agronomic crops which can be commercially grown both under greenhouse and field conditions, while it has been noted that the Marsh Cabbage possesses a high metabolic output in its early stages of growth, R. M. Knutson, *Science* 186: 746–747 (1974). In view of the hypothetical model set forth in the discussion following the examples herein, and in light of the fact that certain characteristics of the transduced plants in Examples 1 and 2 were intermediate the characteristics of the donor and acceptor species, it was thought there was a significant chance that the high metabolic output of Marsh Cabbage could be imparted to tomato seedlings to increase their fruit yields, and thereby increase the commercial value of the crop.

A number of tomato seedlings so treated were grown in a greenhouse, and the number of plants resulting from treatment, and the number of fruit borne by those plants at the time of fruit ripening, are shown in Table II. Both the positive and negative electrode orientation data were combined in the data reported in Table II, since in this case there were no apparent polarity differences. Again, the asterisk indicates data which is significant at a 95% confidence level (P less than 0.05).

TABLE II

| DONOR | AVERAGE | FRUIT/PLANT AND s.d. | N-PLANTS |
|---|---|---|---|
| Macerate | *4.33 | (2.64) | 15 |
| Controls | 2.43 | (2.42) | 21 |

This same donor/host transduction was repeated for the purpose of examining yield levels under field conditions. Using three different varieties, a total of 24 test series were prepared with 30 transduced seedlings in each series (15 per electrode polarity) plus 15 control, non-transduced plants. Exposure was again conducted with the apparatus shown in, and the method described in conjunction with, FIG. 3, at a direct current potential of 9 volts and an exposure time of five minutes. All plants were handles and reared under similar conditions of field environment. Yields from individual plants were recorded at the time of optimum fruit harvest (approximately two-thirds mature fruit per plant).

Of the 24 test series, 7 of them, or 29.2%, disclosed a statistically significant yield advantage (based on mean weight of fruit per plant) over the control or non-transduced groups, at a confidence level of 95% (P less than 0.05). Within the groups showing yield increases, there were also concomitant, statistically significant increases in growth rates and in plant size. The yield data possessing this significance ranged from +35% to +70% fruit weight increases over the controls. An experienced plant geneticist and breeder observing the transduced series selected one with a +50% (P less than 0.05) yield increase as having improved phenotypic characteristics for traits desirable for commercial harvesting, specifically, upright plants having good clustering of fruit.

Individual plants were selected and grown in T2 generation field replications as plant rows (30 plants per row) from this particular exceptional plant series as well as from several of the T1 generation series, including some that showed no yield advantages. Yields were again recorded in the T2 generation. These plants row data disclosed that those plants showing growth and yield advantages in the T1 generation also gave high growth rates and yields in the T2 generation, whereas those showing no growth or yield advantages in the T1 generation gave no growth or yield increases in the T2 generation. From the T1 generation exceptional progenitor plant, a total of 10 plant rows gave statistically significant yield advantages ranging from +40.7% to +55.6%, compared with the T2 generation control plant yields. T3 inbred generations of these high yielding plants are currently being compared in several large scale field tests (approximately five acres at four different locations) with two high yield commercial varieties, as well as with the non-transduced F3 generation controls. In all locations the transduced line is still showing significant growth and development advantages over the non-transduced varieties.

This example illustrates the consistency of the induced phenotypic effects and practical increases in the rates of fruit production in a commercially valuable crop, when the method of the present invention is practiced.

EXAMPLE FIVE

The *Symplocarpus foetidus* root tissue used as donor material in Example Four was prepared in the early spring (mid-March) growth period, when the metabolic activity in the root was at a high rate. Donor tissue prepared from different tissue regions of the donor plant and taken at a later stage of maturity can have significantly different effects on the growth rate in the acceptor plant *Lycopersicon esculentum*. Tissues from the root, the development spadix in the lower stem of the plant, and the leaf foliage of the Marsh Cabbage were collected in mid-April, and donor macerates were prepared as described in Example Four and shown in FIG. 3. Seedlings from four different commercial and established varieties of tomato plants were treated with these macerates and with a direct current 9 volt potential and five minute exposure. The tomato seedlings were grown under greenhouse conditions and periodic growth data was obtained. Table III presents data obtained at six weeks of growth which shows the percentage of the total series which possessed growth statistically significantly higher (P less than 0.05) than the corresponding control series.

TABLE III

| DONOR TISSUE | TESTS WITH SIGNIFICANT GROWTH | N-TEST SERIES |
|---|---|---|
| Root | 2.8% | 36 |
| Spadix | 19.4% | 36 |
| Foliage | 30.0% | 20 |

The foliage employed as a donor, with its high rate of protein synthesis, yielded the highest percentage of tests showing significant growth increases in the acceptor series, when compared with the controls. It is noteworthy that the root macerate used in the above test produced significant growth increases in only 2.8% of the series, whereas in Example Four the root tissue obtained about one month earlier (when at its high level of metabolic activity) induced high growth in 29.2% of the test series.

This example serves to illustrate the importance of the selection of tissue for the transduction donor, as well as considering its state of maturity.

EXAMPLE SIX

Many varieties of plants in the pea and bean family (legumes) have the ability to more efficiently utilize or fix nitrogen from the atmosphere than other plants. This diazotrophy occurs through bacteria which live symbiotically on the plant roots and form outgrowths or root nodules. The results of this example suggest that an acceptor species in the cereal family such as corn, which does not fix nitrogen, could have mutations and growth stimulation induced therein from a donor bean species which has these root nodules.

A donor extract was prepared from soy bean (*Glycine max*) root nodules excised from plants grown from seeds which were initially inoculated with the bacterium *Rhizobium japonicum*, which is known to produce diazatrophy in soy beans. The macerated nodule liquor was mixed uniformly with agar as a base, and corn (*Zeas mays*) and sunflower (*Helianthus annuus*) seedlings were both treated with this donor extract in fashion shown in and described in conjunction with FIG. 3.

EXAMPLE SIX (A)

Both corn and sunflower seedlings were placed in the base medium and exposed to a potential giving an initial current of about 30 microamps through the seedlings. After exposure the seedlings (along with equal numbers of controls) were planted in a field test plot, with no fertilizer added. Growth and development studies were conducted on three separate test series of corn and two separate test series of sunflower seedlings. The growth and development enhancement produced by the root nodule extract treatment was consistently observed in all five test series. Examples of growth and development data are presented in Table IV for a field test series of corn and in Table V for a field test series of sunflower plants. The corn seedlings were exposed to the current for one hour, with the cathode inserted into the donor medium; the data of Table IV were obtained from twelve plants in each series. The sunflower seedlings were exposed to the current for 30 minutes, with the cathode inserted into the donor medium; the data of Table V were obtained from twenty plants in each series. The differences in growth shown in the last column of each table were significant at the 99% confidence level (P less than 0.01).

mercially available inbred varieties, Mo17-Ht, A634-Ht, A632-Ht, B73-Ht and W117-Ht, and thus provided range of different lines of stable but homozygous test material. The use of different inbred lines also provided a germ plasm for subsequent hybrid crossing studies.

A total of 18 test series were prepared and examined under field conditions in accord with this protocol. The observed development alterations in the T1 generation were primarily in the rates of maturity or tassel development, in growth rates and in changes in root structure and morphology. The roots in several of the treated series disclosed a much more branching or dendritic patterning, with thickening at the terminus of the root. The roots of the control plants had less branching with no thickening at their termini. This formation of inchoate nodules and alterations in the root morphology of the corn plant is indicative of the initial stages of diazotrophy induction in this cereal plant. Plants from those groups disclosing significant increases in the rate of

TABLE IV

| DAYS AFTER PLANTING | ROOT NODULE EXTRACT AVE. | S.E. | CONTROLS AVE. | S.D. | GROWTH DIFF. |
|---|---|---|---|---|---|
| 7 | 9.25 cm | 2.14 cm | 5.09 cm | 1.64 cm | +81.7% |
| 19 | 47.00 | 6.41 | 31.45 | 8.89 | +49.4% |
| 31 | 83.58 | 9.99 | 64.64 | 16.83 | +29.3% |
| 46 | 104.92 | 13.14 | 80.45 | 19.44 | +30.4% |
| 62 | 109.00 | 25.04 | 74.64 | 37.37 | +46.0% |

After 73 days of field growth, the root nodule group disclosed an 84% near development and the control group only a 16% ear development. After 90 days field growth, the average ear weight of the root module series was 55.0 g and the average ear weight of the control series 28.7 g. The kernals on the treated series were also more fully developed than were those of the controls.

tasseling or growth were then selected on an individual plant basis for T2 generation self pollination. These T2 general plants were then used in T3, T4 and T5 generations, for both inbred and hybrid crosses.

The advantage of the use of genetically pure, homozygous inbred varieties or lines as the acceptor materials is that mutations in corn can be keyed to alterations in particular chromosomes from known listings. Specifi-

TABLE V

| DAYS AFTER PLANTING | ROOT NODULE EXTRACT AVE. | S.D. | CONTROLS AVE. | S.D. | GROWTH DIFF. |
|---|---|---|---|---|---|
| 10 | 8.00 cm | 1.56 cm | 6.00 cm | 1.81 cm | +33.3% |
| 22 | 20.30 | 3.15 | 16.00 | 3.89 | +26.9% |
| 37 | 67.00 | 10.87 | 56.25 | 11.18 | +19.1% |
| 53 | 103.10 | 16.41 | 86.90 | 18.17 | +18.6% |

At maturity the mean seed pod weight (before seed removal) of the nodule-treated group was 21.7% higher than the mean seed pod weight of the control group.

In these field test series, the polarity conditions were limited to the donor medium electrode being the cathode. The reason for examining only the one polarity condition was the fact that preliminary studies with the soybean root-nodule extract disclosed a greater growth response with the donor medium media electrode being negative than with the medium electrode being positive.

This example shows the induction of more efficient growth, development and yield from the root-nodule extracts, as compared to the control plants.

EXAMPLE SIX (B)

Corn seedlings were placed in the donor medium and exposed to a direct current 15 volt potential giving an initial current in the range of 30 microamps through the seedlings. After 10 minute exposures, groups of 15 test seedlings along with equal number of controls were planted in a field test plot, no fertilizer added, and growth data taken periodically during the growth cycle. The test was conducted with five pure and comcally in the case of corn, new genotypic and phenotypic expressions can be compared with those listed in *The Mutants of Maize*, N. G. Neuffer, et al Crop Science Society of America (Madison, Wisc.), 1968; and *Maize for Biological Research*, W. F. Sheridan, Ed. Plant Molecular Biology Association, (University Press, N. Dak.), 1982. It is well known to those skilled in the art that if a particular characteristic appears in a subsequent generation of a plant line where this characteristic was not previously present, a point mutation has occurred on a particular chromosome. Indeed, these point mutations are cataloged in this fashion.

The treatment of corn seedlings by the present invention with the soybean root module donor material produced a number of changes in characteristics in the T2 generation which are known to be associated with particular point mutations. In particular, a number of these mutations are known to be located on chromosome-3, which occurred in the T2 generation plants obtained from some of the treated series. A summary of the frequency of mutations found in two of the inbred treated series (derived from the A632-Ht acceptor) are listed below in Table VI. There were no mutations or phenotypic alterations (a zero percent level) observed in several thousand control or non-transduced plants from this same inbred line.

TABLE VI

CHROMOSOME-3 POINT MUTATIONS
(T2 GENERATION FROM TRANDUCED INBRED A632-Ht)

| MUTATION | SERIES M33-1-18 | SERIES M33-1-7 |
|---|---|---|
| Dwarf | 7 (20%) | 0 |
| Short | 7 (20%) | 0 |
| Dwarf-Crinkly Leaf | 5 (14%) | 13 (30%) |
| rinkly Leaf | 0 | 8 (19%) |
| Short-Romosa | 0 | 8 (19%) |
| Dwarf-Crinkly-Romosa | 0 | 1 (2%) |
| Normal | 16 (46%) | 13 (30%) |
| TOTAL PLANTS | 35 | 43 |

The probability of any one of these mutations occuring in one plant by change alone is about 1 in 500,000 whereas in Table VI there are shown several cases in which a number of plants expressed two mutations and in one case, a single plant expressed three mutuations. Now, from the laws of strict probability, the odds that these percentages occurred by random chance are, in the case of two mutations on the same plant, one in $2.5 \times 10^{11}$ and, in the case of three mutations on the same plant, one in $1.25 \times 10^{17}$. In addition to point mutuations, other transduced series were observed to express large increases in point mutuations which are known to involve several gene alleles. Examples of these multiple allele mutuations are listed below in Table VII.

TABLE VII

| TRANSDUCED SERIES PLANTS | MUTATION | | | |
|---|---|---|---|---|
| | ALBINO | LUTEUS | VARIEGATED | TOTAL |
| MED. 27 (A632-Ht) | 26% | 27% | 0 | 144 |
| MED. 25 (A632-Ht) | 0 | 0 | 10.7% | 28 |
| CONTROLS (A632-Ht) | 0.024% | 0.037% | 0% | 8179 |

The data of Table VII show a mutuation increase for both albino and luteus of about a thousand times the level observed in the control population. Many of these mutations are not of commercial interest. For example, albino plants do not produce chlorophyll and expire before maturity. However, there were other mutations which have importance in plant breeding. The dwarf plants listed in Table VI are an example of a useful mutation. These plants are about one half the height of the control plants, but the ear size and production were comparable to those of the controls. This normal ear size on the mutuant dwarf plants is an important and commercially beneficial distinction from dwarf corn plants derived from conventional breeding programs, the difference being that the ears on the conventionally bred dwarf plants are small when compared with the normal hybrid ears, and have large areas on the ears which do not develop kernels at all.

Field studies of dwarf plants obtained from corn seedlings treated in accordance with the method of the present invention establish the existence of a number of commercially important characteristics. The following has been shown to be true from five generations of field trials:

The inbred, dwarf mutants have held their recessive characteristics through the T5 generation and exhibit a 50%-60% reduction in plant height, when compared with untreated parent inbred control corn plants, yet produce full ears of normal size, as compared to the controls.

Using this same method and the same soybean root-nodule macerate as the donor material, the dwarf traits have been produced in treated series from four of the five original inbred varieties.

When T5 generation dwarf plants originating from two different treated inbred lines are crossed in a normal manner to produce a hybrid, the dwarf characteristics are transferred to the hybrid. The resulting hybrid is uniformly about 40% of the height of the hybrid resulting from a cross between two untreated, inbred parent lines.

The ear size and kernel formation in the dwarf hybrids are about the same as in the untreated hybrid controls. The commercial significance of this is that a smaller plant size in the dwarf hybrid allows a higher plant density under field planting conditions, which in turn results in a higher yield per acre.

Lastly, the ears on the dwarf plants are located much lower on the plant than on the normal or control hybrids, and thus are more efficiently harvested than those on taller control plants.

Additionally, a male sterile, cytoplasmic mutation (Cms) was observed in 100% of the plants in one of the transduced, Mo17-Ht inbred lines. This mutation is commercially important in the development of inbred lines which do not require the laborious task of de-tasseling in the normal production of hybrids.

In the T3 generation, a number of plants selected for phenotypic growth and yield advantages were used for hybrid crossing studies. In general, the early development and high yield traits present in the T3 generation plants were transmitted into the hybrids when the treated progeny were expressed through the female line of the hybrid. An example of this is a soybean root-nodule donor series expressing the mutuation "prolific", which relates to the percentage of plants with multiple ears. A normal hybrid line has about a 10% level of prolific plants. In hybrid crosses, using female parents from T2 generation inbreds, a direct correlation was observed between the percentage of plants with prolific mutations and the resulting yields. The yields from three field replications were compared with a good producing commercial hybrid. The yield from one of these high producing treated lines is compared with the control hybrid in Table VIII below.

TABLE VIII

| HYBRID SERIES | PROLIFIC | YIELDS (g/plant) | YIELD INCREASE |
|---|---|---|---|
| Control (HL2454) | 8% | 200.09 | — |
| Female Transduced | 47% | 257.87 | +28.9% (P < 0.05) |

This example illustrates the number and type of mutations which can be induced by the methods of the present invention. Many of the mutuations have utility in the production of new varieties and in the hybridization of plants. The useful mutant characteristics are selected from the test populations by conventional segregation testing methods commonly employed by plant breeders. The useful mutations are also expressed when employed in hybrid crosses.

EXAMPLE SEVEN

As noted in Example Six, the Eastern Marsh Cabbage (*Symplocarpus foetidus*) has a high metabolic output during early spring growth, the result of which is development of the plant during a period of temperatures too low for growth to proceed in most plant species. This metabolic response can be imparted to corn (*Zea mays*) by the method of the present invention, when a donor extract from Marsh Cabbage is applied to the corn seedlings. Potential benefits of such a characteristic might be expressed as higher yields, faster development rates or other useful mutations. A new variety with some or all of these attributes could be grown in regions of the world where the growing season is conventionally believed to be too brief for corn development.

EXAMPLE SEVEN(A)

A donor medium was prepared from the macerated roots of the Easter Marsh Cabbage, and corn seeds were exposed to a direct current during initial inhibition with the medium with the apparatus shown in, and by the method described in conjunction with, FIG. 8. After treatment, the extract-exposed and control series were examined under field growth conditions. Table IX discloses growth data taken just before mid-maturity (36 days after exposure). Each series contained 16 plants. Only the series having a positive base plate polarity during exposure of the seeds exhibited a statistically significant increase (P less than 0.05) in growth, as compared to the controls.

TABLE IX

| BASE PLATE POLARITY | PLANT AVE. | GROWTH S.D. | PERCENT CHANGE |
|---|---|---|---|
| (−) | 0.878 | 0.284 | +9.5% |
| (+) | 1.003 | 0.234 | +25.1% |
| Controls | 0.802 | 0.134 | — |

The polarity differences shown here are consistent with those mentioned in Example Six(A). With the base of the apparatus being the positive electrode, the embryo or radicle end of the seed was disposed upwardly, in contact with the cathode. This arrangement is the one which exhibited a statistically significant increase in plant growth. Cathode-radicle exposure was also the optimum situation for the plant series reported in Table IV and V. This demonstrates the consistency of the electrode orientation in the method of the invention.

A detailed field examination of the plants listed in Table IX disclosed five unique plants out of each group of 16 treated series. Each of these five plants had definite growth enhancement, larger and greener foliage, the foliage being more pronounced than even the other members in the same test series. The growth of these designated "sub-groups" are listed in Table X, again at 36 days after exposure. The differences in growth between the sub-groups and the controls were statistically significant (P less than 0.01).

TABLE X

| SUB-GROUP POLARITY | PLANT AVE. | GROWTH S.D. | N-PLANTS | GROWTH DIFF. |
|---|---|---|---|---|
| (−) | 1.208 m | 0.039 m | 5 | +50.4% |
| (+) | 1.238 | 0.070 | 5 | +54.4% |
| Controls | 0.802 | 0.134 | 16 | — |

Displayed in Table XI are data showing the differences between the leaf blade width in the two sub-groups and the controls. These data were taken at nodes 6 and 7 at 106 days of maturity. The differences in leaf width between the treated and control series are statistically significant (P less than 0.01).

TABLE XI

| SUB-GROUP POLARITY | MAX. AVE. | LEAF WIDTH S.D. | N-LEAVES | WIDTH DIFF |
|---|---|---|---|---|
| (−) | 9.29 cm | 0.91 cm | 16 | +15.6% |
| (+) | 9.44 | 0.87 | 16 | +17.4% |
| Controls | 8.04 | 0.79 | 16 | — |

Development was also more rapid in these sub-group plants. At 82 days development, both sub-groups disclosed 100% tassel formation, whereas in the controls only 37% possessed tassels. The positive polarity sub-group also disclosed two developing ears, with no ear development at all in the controls.

The final yield results for each entire series of plants is shown in Table XII. The ear weights are somewhat lower than normal, especially in the control series. This was due to a dry period during early ear development, a situation which occurred throughout the Midwest in the 1983 growing season. All three series were, however, subjected to the same water stress conditions. The data in Table XII show the importance of early ear development in the two test series which occurred before the water stress interval.

TABLE XII

| BASE PLATE POLARITY | EAR WEIGHT AVE. | S.D. | WEIGHT DIFFERENCE |
|---|---|---|---|
| (−) | 78.5 g | 51.3 g | +187.6% |
| (+) | 131.4 | 80.2 | +381.3% |
| Controls | 27.3 | 24.2 | — |

The final ear weights from the two sub-groups of special high vigor plants gave values of 134 g per ear for five negative base plate polarity plants, and 230 g per ear for the five positive base plate polarity plants. The controls averaged only 27.3 g per ear. The differences are significant at a 99% confidence level (P less than 0.01).

This example demonstrates the induction of a metabolic response having a positive effect on both development and yield in corn, when the corn seeds are treated in accordance with the method of the present invention. It also shows the practical value of selecting outstanding plants in a given test series.

EXAMPLE SEVEN(B)

A donor medium was prepared in mid-March from the macerated roots of the Easter Marsh Cabbage. Corn seedlings were exposed to the donor macerate with the apparatus shown in, and in accordance with the method described in conjunction with, FIG. 3, and with the test conditions described in Example Six(B). The same five inbred lines, also as described in Example Six(B), were utilized. After exposure the treated and control series of plants were examined under field test conditions as outlined in the previous examples.

In the T1 generation, the plant alterations in the treated series of plants were expressed as increased development rates, plant size and plant shape variations. From these treated series of plants, individual plants were selected for T2 to T3 generation inbred and hybrid crosses. In the T2 generation, several point mutations were observed, and their degree of expression is listed in Table XIII, along with the associated allele and chromosome on which the mutuation is known to occur. None of these mutuations was found in several thousand untreated controls.

TABLE XIII

| NAME | MUTATION ALLELE | CHROMOSOME NO. | RECENT EXPRESSION |
|---|---|---|---|
| Rust Resistant | Rp | 10 | 100% |
| Zebra Necrotic | zn | 10 | 10% |
| Purple | pl | 6 | 50-100% |
| Pigmy | pv | 6 | 25% |
| Male Sterile | msl | 6 | 90% |
| Defective Endosperm | de16 | 4 | 25% |

From this list there are three point mutations of utility in the commercial production of hybrids, namely, rust resistance, pigmy and male sterile. The pigmy plants are of quite different phenotype (narrow leaf and other known characteristics) from the dwarf mutants discussed in Example Six(b). However, they could be utilized for a similar purpose, to produce smaller sized hybrids and provide higher plant densities with higher yields. The utility of male sterile plants was discussed in Example Six(B) as well.

In addition to the mutations listed in Table XIII, two important phenotypic alterations were observed which continue to be expressed into a T5 generation currently under study. One new trait involves a line with a maturity which is 12-14 days earlier than the untreated controls. The second is a "broad leaf" expression with leaf widths on the treated lines over 40% greater than those on the untreated controls. The useful nature of the broad leaf characteristic lies in the ability of the plant to receive and utilize more radiant energy per unit time during photosynthetic activity. The result is plant with a more efficient and higher biomass output.

A number of treated series from both the early and broad leaf lines were used in hybrid crossing studies. These plants were selected for either enhanced growth or for altered plant size. When the female line was the treated series, a number of statistically significant yield increases and early maturing lines were observed in the replicated field tests.

This example and previous examples together demonstrate that different donor materials produce significantly different mutations and phenotypic growth responses, as may be seen by comparing the point mutations in Example Six(B) (resulting from soybean root nodule donor material) with those in this example, employing *Symplocarpus foetidus* as the donor material. New germ plasm is constantly of importance in commercial plant breeding programs and Examples Six(B) and Seven(B) illustrate that although the advantageous expression of a mutation, such as male sterile, may produce similar results, the fact that different alleles are involved in the two examples means that the characteristics in the germ plasm would be expressed quite differently in hybird usage.

CONTROLS

In order to insure that the results obtained in these examples resulted from the combination of subjecting the acceptor species plants to electrophoretic conditions and to whole cells and associated materials of a second species of plant, controls were conducted in which the materials of the second species of plant were replaced by distilled water or by a macerate of plants of the same species as the first species. Additionally, seedlings of the same species had root portions excised and joined together, as well as being exposed to an electropotential difference only. In all cases, no statistically significant difference was seen between any of the plants so treated and untreated control plants. Thus, the results obtained in the examples described in this application necessarily resulted from the inclusion of a donor material from a second, different species of plants.

DISCUSSION

The data obtained in the above examples leads to the inescapable conclusion that the frequency of plant mutations can be increased by exposing plants in their germinal phase simultaneously to electrophoretic conditions and to the whole cells and associated materials of a second species of plant. The fat that some of the mutated plants obtained possess characteristics which appear to be characteristics associated with the donor material of the second species of plant suggests that some genetically associated cell tissue components or macromolecular complexes from the donor species of plant are transferred to or transduced into the intact living cells of the acceptor species of plant, in such a manner as to alter the genotype and/or phenotype of the acceptor, to allowing such altered genetic and phenotypic characteristics be transmitted to successive generations as point mutations or as cytoplasmic transmitted traits. The subsequent discussion and examples supporting such a theory should be taken as evidence of the theory; however, the theory of transduction of genetic materials is not in and of itself essential to an understanding of or a practice of the methods of the present invention. Those methods have been demonstrated by the preceeding examples to be useful in producing an increased number of mutants in a plant population, without regard to whether the instant explanation of how such mutations occur is correct. The fact that the mutations occur is sufficient support for the invention.

The theory as to how the present invention operates is straightforward. It is believed that in the present invention the application of electrophoretic conditions to the cells of an intact organism or whole plant allows the tranduction of genetically associated cell tissue components and macromolecular complexes from the donor species material to the recipient plant species. Migration of these materials would be induced by transmembrane ionophoretic currents, either arising from the natural difference in membrane potentials between cells of different species, or from an externally applied current. The theoretical feasibility of electrophoesis occurring laterally or along, but not through, cell membranes, has been discussed by Jaffe, *Nature*, 265: 600–602 (1977), and was demonstrated experimentally within the cell membrane and wall by Woodruff and Telfer, *Nature*, 286: 84–86 (1980). However, as opposed to the present invention, this ion migration was observed and performed by the injection of fluorescent trace-proteins through the cell membranes of an insect ooctye, where they were observed to migrate laterally along "intercellular bridges" or openings, but was not transferred through the membrane barriers without breach of them. Quite simply, the advantage of the present invention is the fact that it is conducted with normal, intact cells of the acceptor species, and at worst with tissue macerates of the donor species. The need to breach or remove the cell wall encountered in all previous techniques is avoided.

Figure 10A:
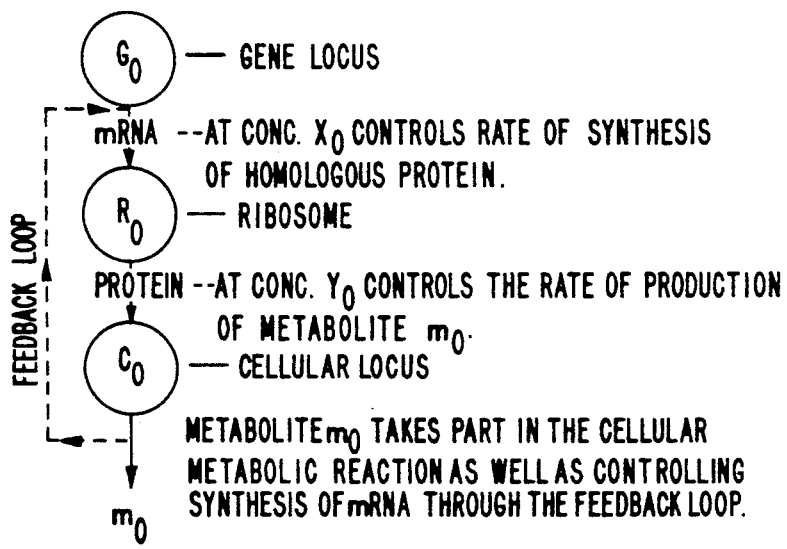
FIG. 10A is a graphic representation of a homeostatic pathway model of the changes induced in plants of a first species by the method of the present invention.
Figure 10B:
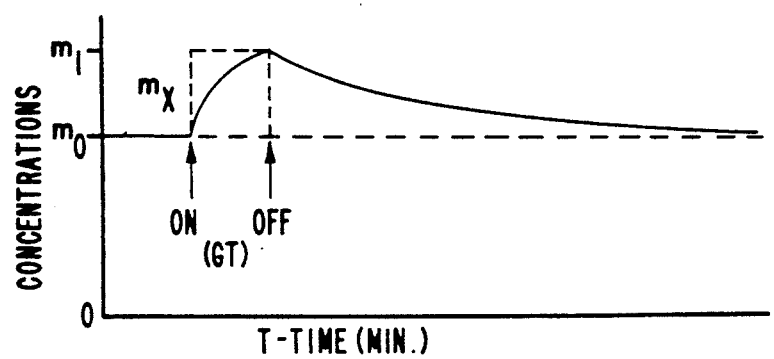
FIG. 10B is a graphic representation of the response of the concentration of a hypothetical metabolite when a homologous metabolite from a different plant species is introduced into the cell when the method of the present invention is carried out.

Electrophoresis can alter cell plasmalemma permability. This permability is changed by altering the size or current of charge carrier proteins and micropores in the plasmalemma and nuclear envelope. And, as demonstrated by the subsequent examples, it is also clear that the application of electrophoretic conditions allows the ready passage of nongenetic materials through the normal, intact cell wall. Additionally, routine commercial gel electrophoresis techniques demonstrate that some sort of genetic alteration is associated with the method of the present invention. The transmission of certain enzymes, mRNA or tRNA from the cells of the donor plant species to the cytoplasm or nucleoplasm of the cells of the acceptor species of plant alter the rate or path of one or more specific biosynthetic pathways in the acceptor species, which would then alter the phenotype of the cells of the plant. A model of such alteration is shown in FIGS. 10A and 10B, and is described further below.

An examination of electrophoretic technology as a testing procedure was conducted in 20 transduced corn lines and five untreated control lines, from which the test lines were derived. All lines were from the T4 generation of field testing. Gel electrophoresis indicated the presence of 10 transduced lines, or 50% of the total test group, having altered gene alleles. All five inbred controls displayed uniform, unchanged electrophoretic patterns. A total of 8 enzymes, out of the 37 known loci in corn, were examined and provided confirmatory evidence of polymorphism or new gene alleles. In a second test series, 12 enzymes were examined. The test group consisted of 42 transduced lines, 21 from each; of two different in-bred host or control lines. The material from the T4 generation again possessed a high percentage, about 28 percent, of transduced lines having altered alleles, with essentially unaltered or homozygous patterns in the untreated control samples.

Applicant has observed that induced dielectrophoretic properties or long range dipole interactions of a donor material can influence the spatial configuration of organelles within the acceptor cells located within the tissue regions of tranduction. For example, when donors are employed which have a strong, positive dipole charge, that is, a dipole moment much higher than that of water, or donors are employed that have been oxidized and thus receive a net positive charge, those donors migrate from the anode region and pass through the plasmalemma, and associated with the cell nucleus, forming a non-uniform electric field having a maximum intensity at the nuclear membrane. This results in an increase in the frequency of the collection of chloroplasts and other cell organelles in distinct proximity with the surface of the nucleus. In normal, untreated tissue, the nuclear-organelle clustering is observed at a low frequency of perhaps 1%-5% of cells, while in transduced tissue, the frequency in limited regions around the electrode contract zone is observed to be as high as 80%-90% of the cells. Chloroplasts and other organelles are clearly attracted to the nuclear membrane by long range dipole interactions.

Applicant has also observed that the chloroplasts and organelles clustering around the nucleus is not a unique property of one specific donor material. For example, other less dipole substances such as distilled water, when used as a donor, do not produce the nuclear-organelle clustering. In the case of a donor which enters the free space (apoplast) of the host tissue and has a marked dipole moment, but is inert with respect to passing through the plasmalemma, the influence on the spatial patterns of chloroplasts is quite different. In such a case the chloroplast and organelle clustering around the nucleus is not observed, but rather the collection of the donor material in the free space of the cells causes a mass migration of the organelles to the cell wall, the direction depending upon the charge characteristics of the donor material. These changes in configural associations caused by electrophoretic conditions greatly increases the probability level for the exchange of genetic information between the nuclear and cytoplasmic DNA, since the organelles are disposed in proximity with the nucleus. The cooperative, long range dipolar effects occur inside the cell through the microdielectrophoretic interactions between the cell organelles. The existence of such dipole interactions has been postulated by Pohl, *Bioelectrochemistry*, Plenem Press, New York (1980). By using a ferroelectric material, specifically, barium titanate, Pohl was able to demonstrate dipolar attraction on the outside surface of animal cells. However, as far as the Applicant is aware, the instant observations are the first time that microdielectrophoresis has been observed inside living cells.

Applicant believes the following mechanism may be an appropriate explanation for the observed migratory phenomenon. It is well known that the plant cell wall contains polysaccharides which act as growth and development regulators and chemical messengers. As noted by Albershime and Darvill, *Scientific American,* September, 1985, page 58, these regulatory molecules are released from the cell wall by enzymes. Different enzymes release different oligosaccharides (small polysaccharides). In a transduction from a new donor species, a donor enzyme complex enters the cell wall matrix and triggers the release of a quite different array of oligosaccharides which, after entering the cytoplasm, redirect patterns of development and form different genotypic associations with either the cell nucleus or the cytoplasmic organelles. As microdielectrophoresis takes place as described above, both nuclear and cytoplasmic interactions occur. This redirection of growth regulators from the cell walls could not occur in the recombinant DNA or protoplast fusion technologies, since the cell wall is necessarily removed in the early stages of the techniques. Further, the enzymes of one plant species may act as isoenzymes of the second plant species and possibly alter the morphogenic properties of the cell. Indeed, there may be enough of a potential difference between the cells of a difference species to facilitate the formation of intercellular cytoplasmic bridges which may allow certain cytoplasmic extranuclear DNA or cell organelles to be transferred from one species of plant to another. The transferred cytoplasmic extranuclear DNA and organelle systems would also exert some influence over the morphogenic determinative components, thereby transforming the phenotype of the tissues.

Additionally, phygocytosis may occur and invaginate certain cell organelles through the cell plasmalemma and into the cytoplasm. Because the cell organelles and cytoplasmic extranuclear DNA synthesize at least some proteins and other materials, which are vital to cell function, the addition of cytoplasmic extranuclear DNA and cell organelles from a different species of pant may cause the creation of enzymes and proteins which are similar enough to the transformed cells' natural products to be utilized by the transformed cell but may, in the process, act as isoenzymes and "isoproteins" which cause the plant to exhibit different phenotypic characteristics, which may then be transmitted to successive generations in a non-Mendelian fashion. For example, in the technique described in conjunction with FIG. 3, the maceration of the donor tissue in distilled water liberates proteins and enzymes inside the cytoplasm of the donor cells, and this can facilitate the transfer of these constituents, because such constituents need pass only from the medium through the cell wall and plasmalemma of the host into the cytoplasm, rather than having to pass through at least two whole cell walls and plasmalemma, as would be the case for non-macerated donors.

The procedures of this invention are believed to involve transductions within the somatic tissues of the host material. The complete expression of a new mutation or phenotypic alteration is not usually observed until at least the T2 generation. For this reason any explanation of what takes place in the host plant after the application of any of the described procedures cannot be based on the concept of a direct, abrupt uptake of donor DNA into the host plant cells during the initial transduction process. The establishing of a fixed genetic expression arising from a transduction appears to be a very gradual process and is believed to occur in a series of stages during the entire cycle of plant development.

For the gradual incorporation of a new genotypic or phenotypic expression into the host plant, the transductions are assumed to be operating within specific biofeedback control systems involved in the plant morphogenesis. To convey this proposed concept of perturbations induced by the genetic transduction process, the least complex of known homeostasis pathways is adopted as a model, B. C. Goodwin, *Temporal Organization in Cells*, Academic Press, New York (1963). In this simple pathway the alteration takes place at a single active gener locus $G^0$, which mormally leads to the synthesis of a cellular metabolite $m^0$ (or enzyme according to the scheme shown in FIG. 10A. In this model, $m^0$ acts as a repressor or co-repressor at the gene site $G^0$ through the feedback loop. The main concern here is with the control of protein (enyzme) synthesis $Y^0$, which regulates the final production of the cellular metabolite.

The assumption is made that the level of the metabolite $m^0$ is perturbed by the introduction into the cell of a homologous metabolite from a different plant species by means of the transduction process. This new metabolite $m^x$ acts at the cellular locus and augments the concentration of $m^0$ so that the new level is at the concentration $m^1$ (FIG. 10B) after the transduction is completed. The rate at which the effect of the transduction $m^x$ is annulled is, for a small perturbation, proportional to the magnitude of the disturbance. From first order chemical kinetics, the level as a function of time t after the transduction is $$m^x = a(e^{-kt})$$

where a and k are constants. A very important point here is that $m^0$ and $m^x$ must be homologous proteins and very similar in their biosynthetic activity in both the donor and host plant systems. if this were not the case, the control loop $m^0$ and repressor level would be unaffected, or in the case of an incompatible metabolite, the entire loop could be inactivated. This could readily explain shy some species are effective as donors and others are not, and why different tissue regions of the same species respond different as donors.

The perturbation of the normal metabolite concentrations $m^0$ to a new level $m^x$ would, through the feedback control, alter the rate of mRNA synthesis at the gene site $G^0$, and a new rate of metabolite production would be established in the tissue of the host plant. As the somatic tissues develop, the entire pattern of gene expression during plant morphogenesis is operating at a different level of temporal organization of nucleotides than would be found in the non-transduced system. As this perturbed, transduced tissue differentiates into meristem regions and ultimately into germ plasm, the kinetics of these altered biosynthetic pathways are transcribed as altered gene alleles, with permanent expression being established in the DNA code. During transcription, the mRNA would contain altered codon sites, which in turn would lead to altered protein synthesis as the polypeptide chains are synthesized on the ribosome surface. Thus we have the situation of the induction of new enzymes synthesized in the epigenetic cycle or enzymatic adaption through the introduction of homologue precursors from another plant species (the donor).

The perturbations of biofeedback control mechanisms within more complex co-repressor systems could account for incomplete or partial masking of dominant alleles in the somatic tissue. In the situation where cytoplasmic mutations arise form the transductions, the inherited alterations may be brought about in quite a different manner. In this case the presence of foreign polypeptides from the donor leads to the possibility that such polypeptides become genetic precursors and may be subsequently imported into chloroplasts and mitochondria, A. Cashmore et al., *Biotechnology*, 3: 803–808, (1895). The plant genome is unstable and capable of generating variability, *Science*, 224: 1415, due to changes in repeated DNA units which are more common in plants than animals (more than 75% of all DNA sequences fifty base pairs or longer is repetitive DNA). Repeated sequences are especially prone to undergo loss or gain because they can promote the incorrect pairing of chromosomes during meiosis. If there are multiple copies of a gene, one copy may be mutated and lead to a new function, as in the above transduction scheme, while the previous function is maintained by the remaining members or copies of the gene. Such copies have the characteristics of transposable elements, B. Mc Clintock, *Science*, 226: 946, with the result that some specialized cells undergo gene activation and phenotype changes. Only DNA loss is irreversible, other DNA alterations such as methylation, chromatin structure, protein-DNA interactions and the like being reversible and modifiable. The mechanisms for all embodiments of this invention are thought to be similar to the above recited model.

Thus, under the application of an electric current across tissues from two different species of plants, transmembrane ion migration occurs, with specific enzymes, their precursors mRNA and tRNA, and regulatory polysaccharides being transmitted from a donor species into the cytoplasm of an acceptor species. Current flow across the tissues also effects the electric charges on the cell membranes and greatly alters membrane permeability and ion pathways through the intrinsic proteins within the cell membrane, which control the transfer of ions and large molecules. With in the cell, microdielectrophoresis alters spatial configurations of the organells, resulting in increased probabilities for the transfer of genetic information between the organells and thereby causing increased rates of mutation. The following examples demonstrate the ready degree of ion migration occuring in cells and germinal plants upon the application of electrophoretic conditions.

EXAMPLE VIII

To elucidate the mechanisms occuring at the cellular level, donors were utilized with known ionic charge characteristics and with both inert and biologically active properties. One type of host tissue consisted of the chlorophyll containing stems of *Pelargonium maculatum*. Stems about 5 centimeters long and 5 to 8 millimeters in diameter were subjected to two to four hours at about 10 to 20 volt potentials and a current density of about 30 microamperes per square centimeter. The negatively charged, red protein pigment from the Amaranth plant was applied as a donor material in the apparatus disclosed in and according to the technique described in conjunction with FIG. 8, with each end of the host stem contacting a pigment-containing electrode. At the cathode end of the test stem the red pigment migrated through the section, leaving a zone of stained tissue extending several millimeters into the stem. At the boundary of this zone of migration, a microscopic examination revealed the stain collecting of the nucleus of the parenchyma cells. At the anode end of the test stem, the pigment was oxidized and because positively charged. As it migrated from the anode end of the stem it gave the host tissue a dark grey color zone extending several millimeters into the stem. At the boundary of this zone, a microscopic examination revealed a clustering or proximal grouping of chloroplasts in the immediate vicinity of the cell nucleus. The oxidized Amaranth was observed to collect on the nucleus, and through long range dipole intractions (microdielectrophoresis) formed a positive electrical field gradient which then attracted the negatively charged chloroplasts to the surface of the nucleus at the locations of maximum field strength.

Confirmation of these dielectrophoretic alterations in spatial configurations of cell organelles was observed when using a powdered form of carbonyl iron having a particle size of one to 10 microns, with a positive electric charge. When transduced into geranium stems, as in the preceeding example, an electrophoretic migration of 1 to 2 centimeters occured at the anode end of the stem. Carbonyl iron is biochemically active and was observed to be transduced into the cell cytoplasm where, as in the case with the oxidized Amaranth pigment, it caused a long range dipolar attraction of the chloroplasts in the cytoplasm. The chloroplasts were found to be more tightly grouped around the cell nucleus than in the case with the cell Amaranth donor. This is explained by the fact that within the same host tissue and under the same conditions of voltage and time, when compared with the Amaranth, the carbonyl iron migrates over two times the distance into the host tissue. This indicates that the carbonyl iron has a higher ionic mobility than the Amaranth pigment.

A donor macerate of *Phaseolus multiflora* leaves containing macromolocules and proteins with associated charge groups, when electrophoretically transduced into the non-chlorophyll tissue of *Zea mays* radicles using the same method as above, causes a clustering of cellular plastids and other cell organelles (too minute to identify microscopically) around the cell nuclei in the anode region of the host tissue. At the cathode region the cell nuclei had a smooth outline and the chromatin structure was uniform. Other less ionic donor substances such as distilled water, when transduced in a similar manner, with the host tissue being either the geranium stem tissue or the non-chloroplast radicle tissue of corn, did not induce the observed spatial readjustments in the cell organelles.

Barium ferrite of particle size 1.3 microns and having a net negative charge was then used as a donor for the purpose of examining a biochemically inert substance which enters only the free space (apoplast) of the host tissue. Using the geranium stem as the acceptor and employing exposures as in the preceeding example, the extent of the migration was far less than when using the more biochemically active materials. The dark stained tissue region was only two to three millimeters into the cathode end of the stem section. At the boundary of the migration, the donor particles cause the negatively charged chloroplasts to migrate and cluster at the cell wall opposite the location of the cathode and migrating barium ferrite. The grouping here was of an entirely different spatial patterning then when using donors which enter the cytoplasm of the cell of the host tissue.

This example serves to teach that in the process of electrophoretic transduction as described in this invention, the donor complex can migrate both through the cell free space of the host tissue, as well as through the plasma membrane into the cytoplasm of the cell. Furthermore, the nature and ionic strength of the molecular dipole charges of the donor can significantly alter the natural, more or less random, spatial distribution of cell organelles in the cells of tissues being electrophoretically transduced. Such altered spatial patterns can greatly influence the probability of the exchange of genetic information between the cell nucleus and surrounding organelles, and thus provide one mechanism whereby mutation rates can be significantly increased. This example also teaches that both organic and inorganic molecular species can enter the plant cell and interact with the organelles in a physical and/or biochemical manner. Components from a macromolecular donor complex produced from plant tissue, also enter the cell and are active in the organelle spatial repatterning.

EXAMPLE NINE

Dry seeds of corn (*Zea mays*) were inserted between the stainless steel electrodes of the apparatus illustrated in FIG. 8. The electrodes were covered with filter paper pads moistened with distilled water. The embroyo end of the seed was placed upward, or opposite the base plate electrode. At a 45 volt direct current potential a sharp, well defined uniform line of black pigment was observed to develop and migrate up the seed if the base plate was anodic or positive, or down the seed if the base plate was cathodic or negative.

Since distilled water has a very low ionic content, charge transport in the seed occurred through the oxidation of the pigment materials (polyphenols) in the test seed. The migration of these oxidation products, as testing indicates, is linear with time. This linear relationship is what would be expected under conditions of electrophoretic migration. An ionic mobility of about $0.54 \times 10^{-6}$ centimeters squared per volt per second was observed, a value which is consistent with the rate of movement of large molecules. Microscopic examination revealed the layer of oxidation products to extend laterally through the tests into the outer layers of the endosperm.

This example provides a graphic demonstration of the movement of large, physiologically related molecules through the plant tissues under conditions of an electrical potential as applied in the methods of the present invention.

EXAMPLE TEN

The frequencies of altered enzyme loci producing polymorphism in corn plants in which *Sympolocarpus feotidus* is the donor are quite different from the frequencies when using the soybean root-nodule extract as the donor. These different allelic responses are exemplified by commercial electrophoresis tests. In 62 transduced lines produced in accordance with the method described in conjunction with FIG. 3, 15 lines were transduced with *Symplocarpus feotidus* as the donor, and 47 lines with the soybean root-nodule as the donor. Table XIV provides a listing of the number of transduced lines containing a specific enzyme polymorph, as they occurred within the two donor test groups. Only those alleles showing positive polymorphism are included in this listing; those observed to have only a slight variation are excluded. The enzymes listed are those in which polymorphism occurred in at least one transduced line.

TABLE XIV

| Enzyme | Number of transduced corn lines showing polymorphism | |
|---|---|---|
| | S. foetidus | Soybean root-nodule |
| ACP (acid phosphatse) | 6 | 11 |
| PGM (phosphogucomutase) | 4 | 1 |
| MDH (malate dehydrogenase) | 1 | 1 |
| PGD (6-phosphogluconate dehydrogenase) | 1 | 0 |
| PHI (phosphohexose isomerase) | 3 | 1 |
| GLU (B-glucosidase) | 1 | 0 |

The data in Table XIV demonstrates that in the soybean root-nodule lines the majority of the alterations take place at the ACP alleles. In the lines with *S. foetidus* as the donor, there were fewer lines with altered ACP alleles and far more lines involving other enzymes. The fact that the two enzymes, PGD and GLU revealed polymorphism in the *S. foetidus* lines (comprising only 24% of the total test series) and not in the root-nodule lines (comprising 76% of the test series) again emphasizes the influence of the donor type on the final genetic response and range of possible polymorphic alterations that might be achieved by using other donor types and combinations.

Whatever the mechanism yielding the mutations observed when the methods of the present invention are employed, the present invention clearly provides methods for increasing the proportion of mutants in plant generations. The method of the present invention are significantly advantageous over the known methods of recombinant DNA and plasmid fusion techniques, for the reasons that the precise genetic structure of the chromosomes mutated need not be elucidated, time and effort need not be wasted in removing the cell walls, and time and effort need not be wasted in attempting to grow whole plants from isolated tissues. Instead, the acceptor plants are whole germinal plants, which after treatment can be grown in any conventional fashion.

Having described my invention, however, many modifications thereto will become apparent to those skilled in the area to which it pertains, without deviation from the spirit of the present invention, as defined by the scope of the appended claims.

I claim:

1. A method for increasing the proportion of altered phenotypes in generations subsequent to at least one progenitor member of a first species of plant, said first species having at least one established phenotype, and said method comprising:

placing said at least one member of said first species in contact with whole cells and associated materials of a second species of plant while simultaneously applying an electrophoretic current across said at least one member of said first species and said whole cells and associated materials of said second species, during a time said at least one member is in a germinal stage; and allowing said member of said first species to develop from said germinal stage.

2. The invention according to claim 1, wherein said placing and applying step comprises excising the root tips of seedlings of both of said first and second species of plants, abutting the cut surfaces of pairs of disparate seedlings, and applying said electrophoretic current across said abutted seedlings; and wherein said development allowing step comprises separating said paired seedlings and growing each of said seedlings to adult plants.

3. The invention according to claim 1, wherein said placing and applying step comprises placing said a least one member of said first species in physical contact with a macerate of tissue of said second species of plant.

4. The invention according to claim 3, wherein said method comprises admixing said macerate in agar, suspending a seedling of said first species in said admixture, and applying said electrophoretic current across said seedling and said admixture.

5. The invention according to claim 4, wherein said first species comprises sunflower and said macerate is prepared from soybean root nodules.

6. The invention according to claim 4, wherein said first species comprises corn, and said macerate is prepared from soybean root nodules.

7. The invention according to claim 1, wherein said method comprises macerating said tissue of said second plant species in water so as to yield a macerate fluid, disposing said fluid between a first cathode and a first anode, applying a potential difference across said cathode and anode, collecting macerate fluid from the areas adjacent said first cathode and anode, contacting the anode-collected macerate fluid with one of either the root or the shoot of a seedling of said first species of plant, contacting the cathode-collected macerate fluid with the other of said shoot and said root of said first species seedling, connecting a second cathode and anode to said anode and cathode-collected macerate fluids, respectively, and applying said electrophoretic current across said seeding and said cathode- and anode-collected macerate fluids.

8. The invention according to claim 7 wherein said first cathode and second anode are a single syringe, and said first anode and second cathode are another single syringe.

9. The invention according to claim 7 wherein said first species of plant comprises soybean, and said tissue of said second species is from the immature fruit of tomato.

10. The invention according to claim 7, wherein at least one of said second anode and said second cathode comprises a disk electrode supporting a filter paper wetted with one of said cathode- and anode-collected macerate fluids.

11. The invention according to claim 10, wherein a single disk electrode and wetted filter paper are placed in contact with the shoot of a seedling of said first species, and a second electrode is inserted into the root of said seedling.

12. The invention according to claim 10, wherein one disk electrode and wetted filter paper are placed in contact with the hilum of a seed of said first species of plant.

13. The invention according to claim 12, wherein said first species comprises corn, and said tissue of said second species is Eastern Marsh Cabbage root.

14. The invention according to claim 8, wherein said first species comprises tomato, and said tissue of said second species is Eastern Marsh Cabbage root.

15. The invention according to claim 1, wherein said elecrophoretic current is applied at a potential difference of from 1.5 to 90 volts.

16. The invention according to claim 15, wherein said potential difference is between 1.5 and 22.5 volts.

17. The invention according to claim 1, wherein said electrophoretic current is applied for a period between five minutes and three hours.

18. The invention according to claim 17, wherein said period of current application is between ten and thirty minutes.

19. The invention according to claim 17, wherein the current density of said applied electrophoretic current is about one to one hundred microamperes per square centimeter.

20. The invention according to claim 1, wherein said at least one member of said first species comprises a germinal plant of said species.

21. The invention according to claim 20, wherein said germinal plant comprises a seedling.

22. The invention according to claim 20, wherein said germinal plant comprises a seed.

23. The invention according to claim 1, wherein said member of said first species comprises an intact cell of said first species.

24. The invention according to claim 1, wherein said member of said first species comprises a protoplast of said first species.

25. A method for increasing the proportion of altered phenotypes in generations subsequent to at least one progenitor member of a first species of plant, said first species having at least one established phenotype, and said method comprising:

placing said at least one member of said first species in contact with whole cells and associated materials of a second species of plant;

making conductive contact between a first electrode and said member of said first species;

making conductive contact between a second electrode and said whole cells and associated materials of said second species;

applying a potential difference to said first and second electrodes during a time said member of said first species is in a germinal stage, adequate to yield an electrophoretic current across said member of said first species and said whole cells and associated materials of said second species; and allowing said member of said first species to develop from said germinal stage.

* * * * *

UNITED STATES PATENT AND TRADEMARK OFFICE
CERTIFICATE OF CORRECTION

PATENT NO. : 5,288,626
DATED : February 22, 1994
INVENTOR(S) : WILLIAM C. LEVENGOOD It is certified that error appears in the above—identified patent and that said Letters Patent is hereby corrected as shown below:

Column 4, line 14, "seedlings" should read --seedling--.

Column 4, line 57, "germinations" should read --germination--.

Column 4, line 65, "mutations" should read --mutants--.

Column 5, line 13, "tophleom" should read --tophloem--.

Column 6, line 3, "soybeam-soybean" should read --soybean-soybean--.

Column 6, line 23, "afixed" should read --affixed--.

Column 6, line 62, "Once" should read --one--.

Column 8, line 67, "plants id" should read --plant is--.

Column 9, line 35, "fund" should read --found--.

Column 10, lines 36 and 37, after "these plants" and before "and these", the following should be inserted --was sweeter than the fruit of the control plants--.

Column 10, line 38, "condition" should read --conditions--.

UNITED STATES PATENT AND TRADEMARK OFFICE
CERTIFICATE OF CORRECTION

PATENT NO. : 5,288,626
DATED : February 22, 1994
INVENTOR(S) : William C. Levengood Page 2 of 5

It is certified that error appears in the above-indentified patent and that said Letters Patent is hereby corrected as shown below:

Column 10, line 39, "abe" should read --be--.

Column 10, line 66, "protophlem" should read --protophloem--.

Column 11, line 34, "occured" should be --occurred--.

Column 11, line 40, "induct" should be --induce--.

Column 11, line 67, "Fig. 5, 6 and 6" should read --Fig. 4, 5 and 6--.

Column 12, line 1, "has" should be --had--.

Column 13, line 19, "handles" should be --handled--.

Column 13, line 42, "plants" should be --plant--.

Column 14, line 59, "Zeas" should be --Zea--.

Column 15, line 30, "near" should be --ear--.

Column 15, line 32, "module" should be --nodule--.

Column 15, line 34, "kernals" should be --kernels--.

Column 16, line 59, "module" should be --nodule--.

UNITED STATES PATENT AND TRADEMARK OFFICE
CERTIFICATE OF CORRECTION

PATENT NO. : 5,288,626
DATED : February 22, 1994
INVENTOR(S) : WILLIAM C. LEVENGOOD It is certified that error appears in the above—identified patent and that said Letters Patent is hereby corrected as shown below:

Column 17, line 11, "rinkly Leaf" should be --Crinkly Leaf--.

Column 17, line 19, "change" should be --chance--.

Column 18, line 23, after "under" and before "field", --regular-- should be inserted--.

Column 19, line 20, "Easter" should be --Eastern--.

Column 20, line 56, "Easter" should be --Eastern--.

Column 22, line 20, "fat" should be --fact--.

Column 22, line 29, "to" should be deleted before "allowing".

Column 22, line 30, after "characteristics" and before "be", --to-- should be inserted.

Column 22, line 55, "electrophoesis" should be --electrophoresis--.

Column 23, lines 5 and 6, "permability" (both occurrences), should be --permeability--.

Column 24, line 53, "difference" should be --different--.

UNITED STATES PATENT AND TRADEMARK OFFICE
CERTIFICATE OF CORRECTION

PATENT NO. : 5,288,626
DATED : February 22, 1994
INVENTOR(S) : William C. Levengood It is certified that error appears in the above-indentified patent and that said Letters Patent is hereby corrected as shown below:

Column 24, line 63, "phygocytosis" should be --phagocytosis--.

Column 25, line 1, "pant" should be --plant--.

Column 25, line 40, "gener" should be --gene--.

Column 25, line 66, "if" should be --If--.

Column 26, line 2, "shy" should be --why--.

Column 26, line 4, "different" should be --differently--.

Column 26, line 32, "form" should be --from--.

Column 27, line 32, "because" should be --became--.

Column 29, line 36, "phosphatse" should be --phosphatase--.

Column 29, line 37, "phosphogucomutase" should be --phosphoglucomutase--.

UNITED STATES PATENT AND TRADEMARK OFFICE
CERTIFICATE OF CORRECTION

PATENT NO. : 5,288,626
DATED : February 22, 1994
INVENTOR(S) : William C. Levengood It is certified that error appears in the above-indentified patent and that said Letters Patent is hereby corrected as shown below:

Column 29, line 37, "phosphogucomutase" should be --phosphoglucomutase--.

Signed and Sealed this

Thirtieth Day of August, 1994

Attest:

BRUCE LEHMAN

Attesting Officer

Commissioner of Patents and Trademarks